United States Patent
Owens

(10) Patent No.: US 6,331,088 B2
(45) Date of Patent: Dec. 18, 2001

(54) TOOTHBRUSH WITH MULTIPLE PUMPING SYSTEMS

(76) Inventor: Zena Elizabeth Owens, 13813 S. Catalina Ave., Gardena, CA (US) 90247

( * ) Notice: Subject to any disclaimer, the term of this patent is extended or adjusted under 35 U.S.C. 154(b) by 0 days.

(21) Appl. No.: 09/756,001

(22) Filed: Jan. 8, 2001

Related U.S. Application Data

(63) Continuation-in-part of application No. 09/397,604, filed on Sep. 16, 1999.

(51) Int. Cl.⁷ ..................................................... A46B 11/04
(52) U.S. Cl. ................... 401/282; 401/35; 15/29
(58) Field of Search .................... 401/17, 24, 34, 401/35, 39, 282, 283; 15/24, 29

(56) References Cited

U.S. PATENT DOCUMENTS

| | | | |
|---|---|---|---|
| 4,274,173 | * 6/1981 | Cohen | 15/28 |
| 4,543,679 | * 10/1985 | Rosofsky et al. | 15/110 |
| 5,020,694 | * 6/1991 | Pettengill | 222/137 |
| 6,233,773 | * 5/2001 | Karge et al. | 15/29 |

* cited by examiner

*Primary Examiner*—David J. Walczak
*Assistant Examiner*—Peter deVore
(74) *Attorney, Agent, or Firm*—Goldstein Law Offices P.C.

(57) ABSTRACT

A toothbrush with multiple pumping systems including a head portion having three rows of a plurality of outlet ports formed therein. The head portion has a plurality of bristles secured thereto. An elongated handle portion removably couples with the head portion. The handle portion has a hollow interior in communication with the hollow interior of the head portion. Three manual pumps are slidably disposed within the handle portion. Three tubes are removably disposed within the head portion and the handle portion disposed between the outlet ports of the head portion and the three pumps. The three tubes hold quantities of liquid toothpaste, mouthwash, and antibacterial rinse.

9 Claims, 3 Drawing Sheets

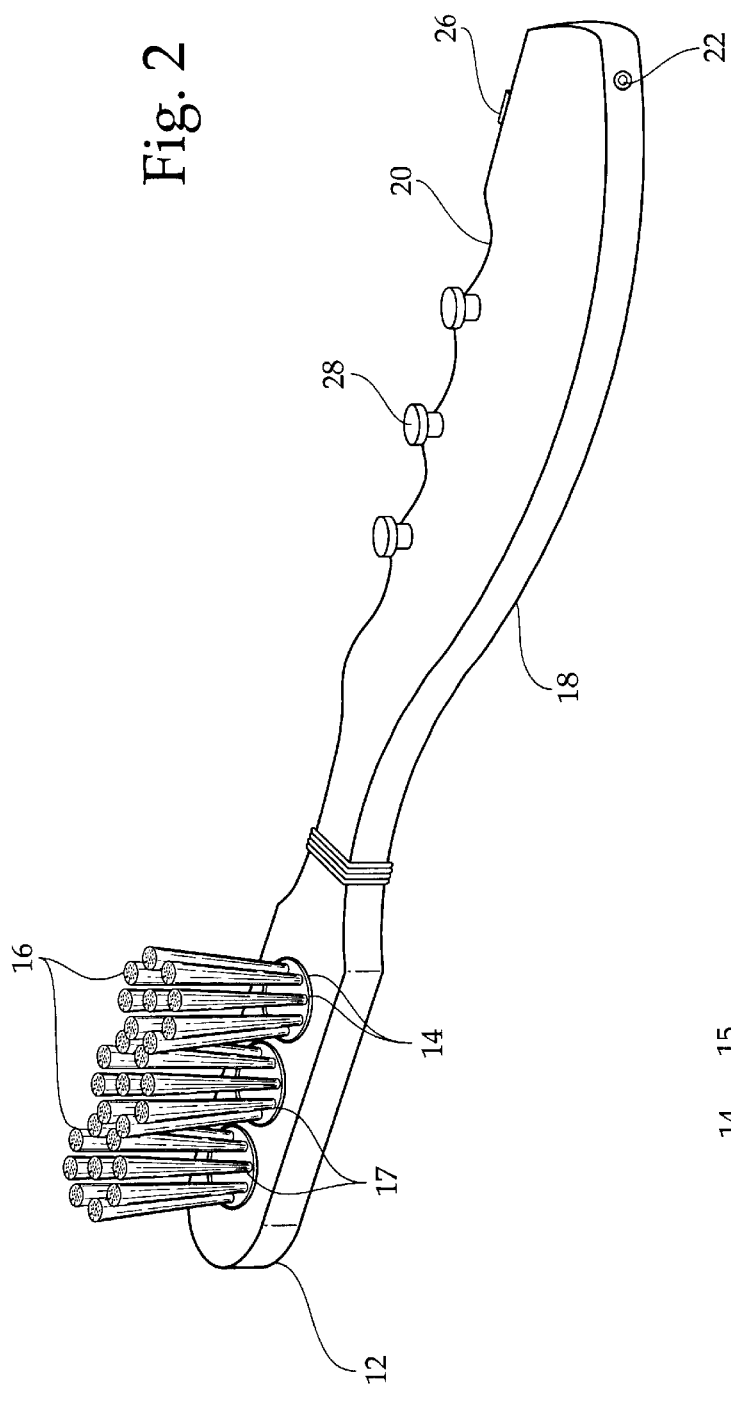
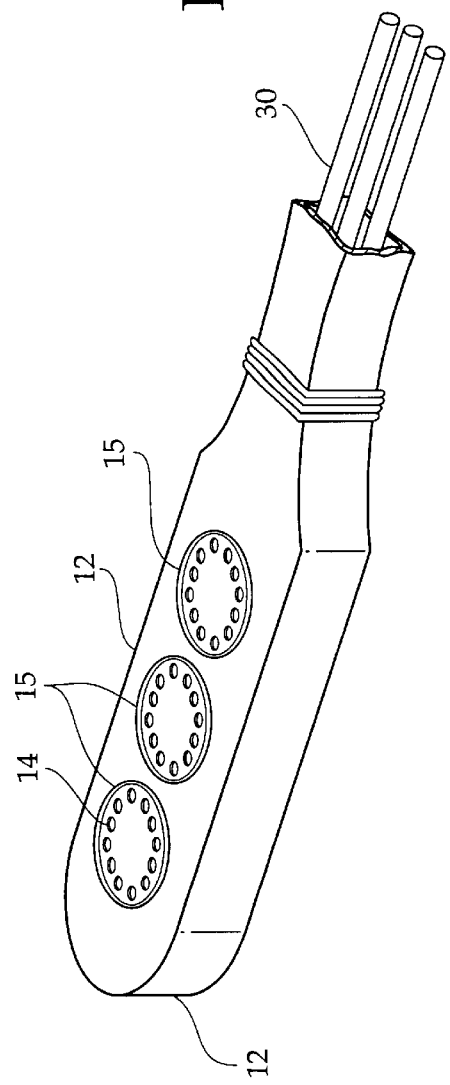

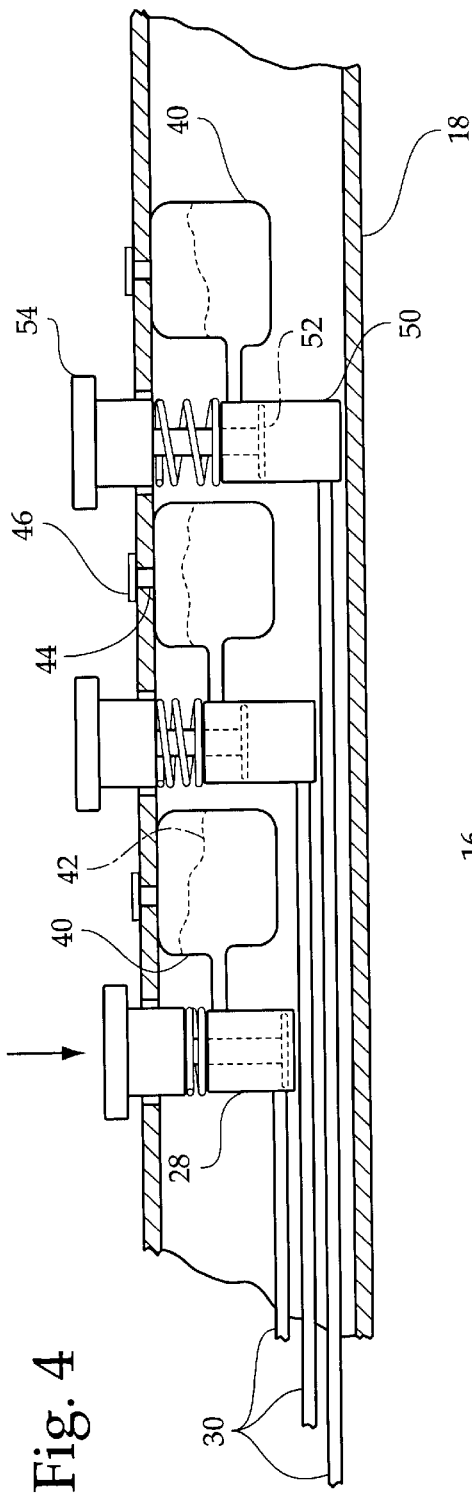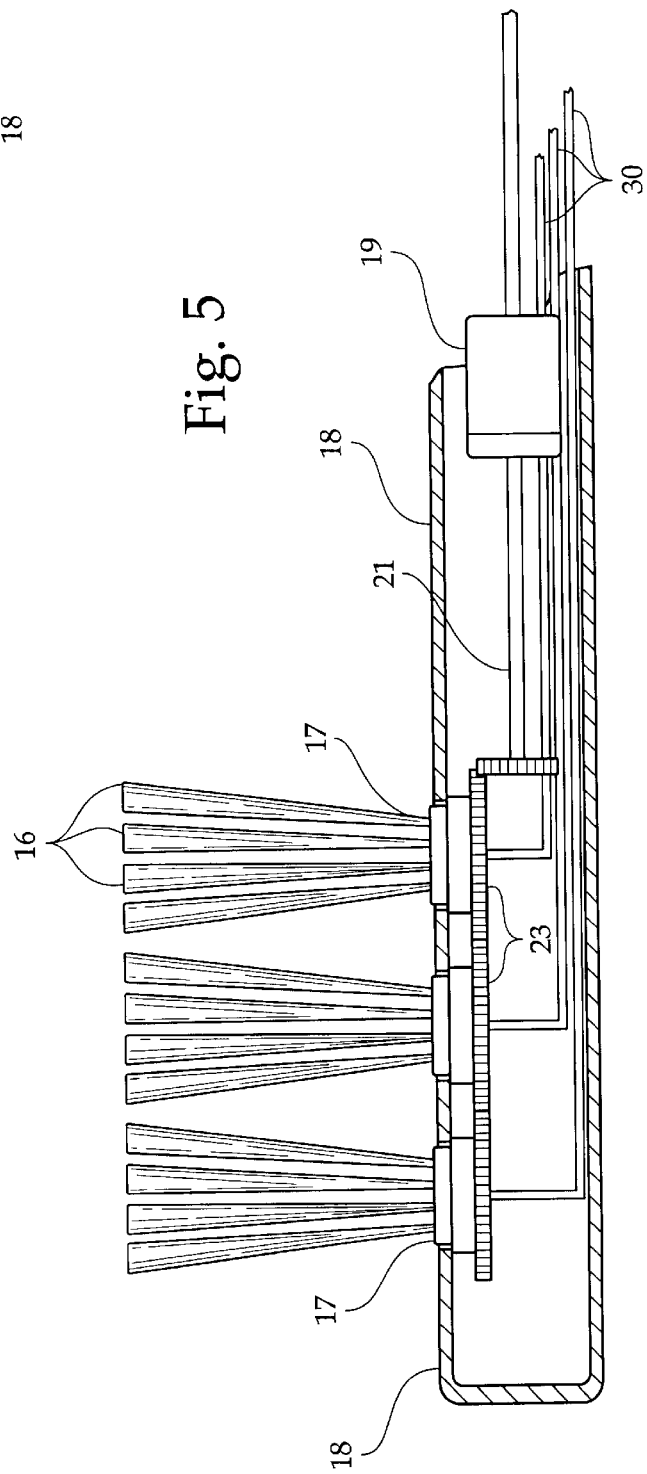

TOOTHBRUSH WITH MULTIPLE PUMPING SYSTEMS

CROSS REFERENCES AND RELATED SUBJECT MATTER

This application is a continuation-in-part of patent application serial number 09/397,604, filed in the United States Patent Office on Sep. 16, 1999.

BACKGROUND OF THE INVENTION

The present invention relates to a toothbrush with multiple pumping systems and more particularly pertains to a toothbrush which selectively dispenses toothpaste, mouthwash, and antibacterial rinse when desired by the user.

People who travel are often restricted with the amount of items that they can carry with them. Most people do not wish to sacrifice the number of personal hygiene items that they use on a daily basis. Thus, a need exists for a device that will incorporate most items that people use for dental hygiene in one simple to use instrument that can also be broken down and easily transported without occupying a great deal of space.

The present invention attempts to solve the above mentioned problem by the providing a toothbrush with incorporated fluid lines and pumps for selectively forcing dental fluids onto the toothbrush or into a user's mouth when required. In addition, the toothbrush selectively dispenses antibacterial rinse onto the toothbrush to sanitize the brush after use. Additionally, this toothbrush can be broken down and stored in an easy to carry case.

The use of dental devices are known in the prior art. More specifically, dental devices heretofore devised and utilized for the purpose of increasing dental hygiene are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,208,933 to Lusting discloses a powered dental tool for cleaning teeth with a supply cartridge incorporated, capable of dispensing a liquid toothpaste. U.S. Pat. No. 5,458,563 to Stewart discloses a toothbrush and pump assembly with a fluid supply and means for fluid extraction, for use by bedridden patients. U.S. Pat. No. 4,017,974 to Sot man discloses a means for spraying water from a dental hand piece. U.S. Pat. No. 2,959,749 to Perry discloses a toothbrush used in conjunction with a water faucet. U.S. Pat. No. 5,170,525 to Cairo discloses a battery operated toothbrush which employs multiple motorized brush groups.

While these devices fulfill their respective, particular objective and requirements, the aforementioned patents do not describe a toothbrush with multiple pumping systems for allowing toothpaste, mouthwash, and antibacterial rinse to be pumped independently from the toothbrush.

In this respect, the toothbrush with multiple pumping systems according to the present invention substantially departs from the conventional concepts and designs of the prior art, and in doing so provides an apparatus primarily developed for the purpose of allowing toothpaste, mouthwash, and antibacterial rinse to be pumped independently from the toothbrush.

Therefore, it can be appreciated that there exists a continuing need for a new and improved toothbrush with multiple pumping systems which can be used for allowing toothpaste, mouthwash, and antibacterial rinse to be pumped independently from the toothbrush. In this regard, the present invention substantially fulfills this need.

SUMMARY OF THE INVENTION

In the view of the foregoing disadvantages inherent in the known types of dental devices now present in the prior art, the present invention provides an improved toothbrush with multiple pumping systems. As such, the general purpose of the present invention, which will be described subsequently in greater detail, is to provide a new and improved toothbrush with multiple pumping systems and method which has all the advantages of the prior art and none of the disadvantages.

To attain this, the present invention essentially comprises a head portion having a generally rectangular configuration. The head portion has a planar upper surface, a planar lower surface and a hollow interior. The planar upper surface has three brush groups which include a plurality of outlet ports formed therein. The planar upper surface also has a plurality of rotating bristles secured thereto. An elongated handle portion removably couples with the head portion. The handle portion has a hollow interior in communication with the hollow interior of the head portion. The handle portion has indentations formed within a side wall thereof. The handle portion has a motor disposed therein in communication with the rotating bristles of the head portion. The motor is powered by recharge able batteries disposed within the hollow interior of the handle portion. The rechargeable batteries have a charging port disposed within the side wall of the handle portion. An adapter couples with the charging port and an electrical outlet for charging the rechargeable batteries. The handle portion has an LED disposed within the side wall for selectively indicating status of the batteries. Three manual pumps are slidably disposed within the handle portion. Three tubes are removably disposed within the head portion and the handle portion disposed between the outlet ports of the head portion and the three pumps. The three tubes hold quantities of liquid toothpaste, mouthwash, and antibacterial rinse. A carrying case is provided that is adapted for holding the head portion, handle portion, adapter, and the three tubes therein. The carrying case contains a spare head portion therein.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved toothbrush with multiple pumping systems which has all the advantages of the prior art dental devices and none of the disadvantages.

It is another object of the present invention to provide a new and improved toothbrush with multiple pumping systems which may be easily and efficiently manufactured and marketed.

It is a further object of the present invention to provide a new and improved toothbrush with multiple pumping systems which is of durable and reliable construction.

An even further object of the present invention is to provide a new and improved toothbrush with multiple pumping systems which is susceptible of a low cost of manufacture with regard to both materials and labor, and which accordingly is then susceptible of low prices of sale to the consuming public, thereby making such a toothbrush with multiple pumping systems economically available to the buying public.

Even still another object of the present invention is to provide a new and improved toothbrush with multiple pumping systems for allowing toothpaste, mouthwash, and antibacterial rinse to be pumped independently from the toothbrush.

Lastly, it is an object of the present invention to provide a new and improved toothbrush with multiple pumping systems including a head portion having three rows of a plurality of outlet ports formed therein. The head portion has a plurality of bristles secured thereto. An elongated handle portion removably couples with the head portion. The handle portion has a hollow interior in communication with the hollow interior of the head portion. Three manual pumps are slidably disposed within the handle portion. Three tubes are removably disposed within the head portion and the handle portion disposed between the outlet ports of the head portion and the three pumps. The three tubes hold quantities of liquid toothpaste, mouthwash, and antibacterial rinse.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a perspective view of the present invention illustrated in an operative orientation.

FIG. 3 is a partial perspective view of the present invention illustrating the head portion with release ports as coupled with the holding tubes of the present invention.

FIG. 4 is a side elevational view, with parts broken away, illustrating the handle portion, liquid storage compartments therein, and their respective pumps and delivery tubes.

FIG. 5 is a side elevational view illustrating the brush groups, and interconnection between the fluid delivery tubes, the motor, and the brush groups.

The same reference numerals refer to the same parts through the various figures.

DESCRIPTION OF THE PREFERRED EMBODIMENT

Figure 1:
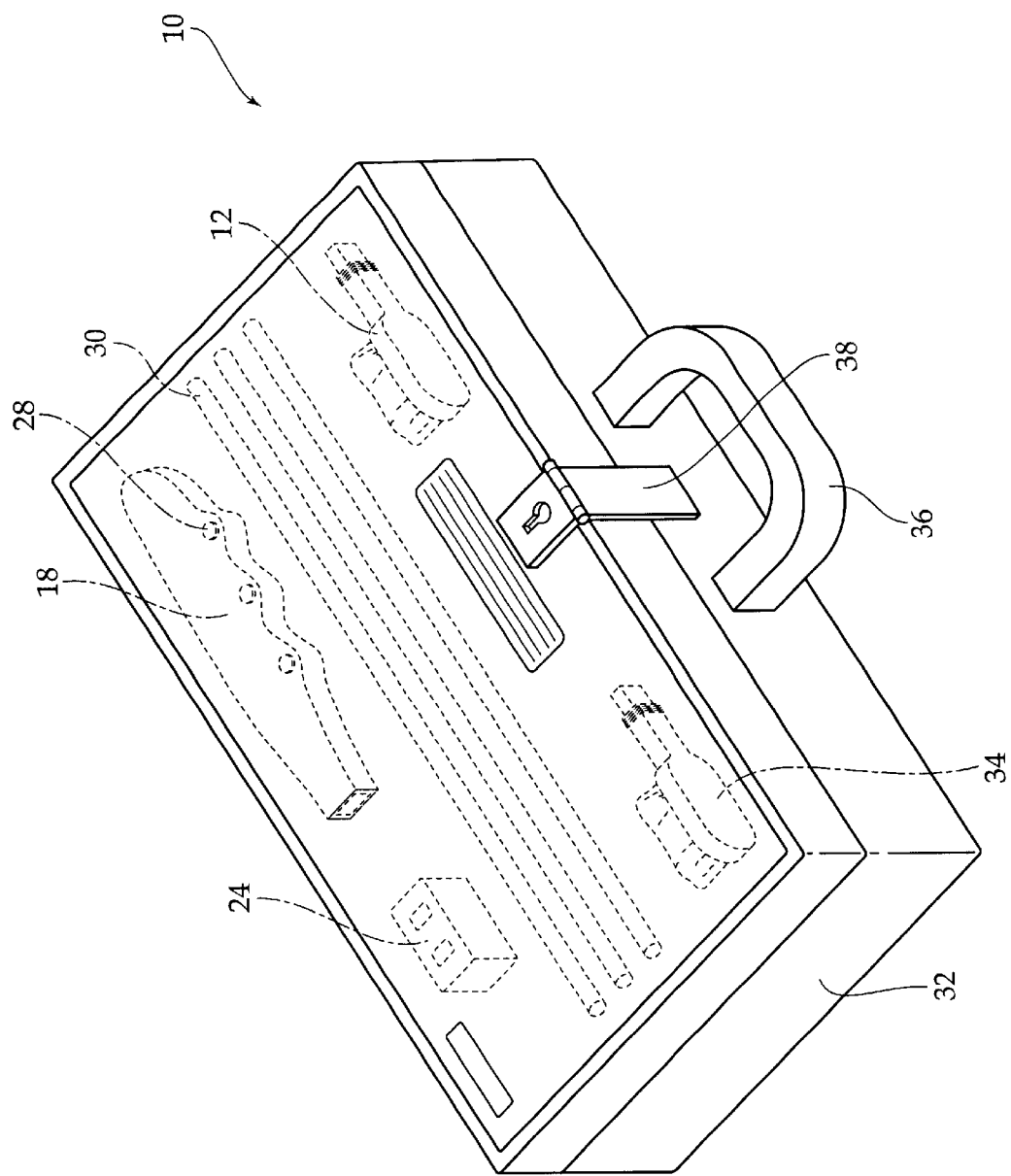
FIG. 1 is a perspective view of the preferred embodiment of the toothbrush with accessories therefor contained within a carrying case.

With reference now to the drawings, and in particular, to FIGS. 1 through 5 thereof, the preferred embodiment of the new and improved toothbrush with multiple pumping systems embodying the principles and concepts of the present invention and generally designated by the reference number 10 will be described.

Specifically, it will be noted in the various Figures that the device relates to a toothbrush with multiple pumping systems for allowing toothpaste, mouthwash, and antibacterial rinse to be pumped independently from the toothbrush by a user. In its broadest context, the device consists of a head portion, an elongated handle portion, three manual pumps, three tubes, and a carrying case. Such components are individually configured and correlated with respect to each other so as to attain the desired objective.

The head portion 12 has a generally rectangular configuration. The head portion 12 has a planar upper surface, a planar lower surface and a hollow interior. The planar upper surface has three rings 15, which each have a plurality of outlet ports 14. Rotating bristles 16 are secured in the outlet ports 14, and together form three rotating brush groups 17.

The elongated handle portion 18 may be made to removably couple with the head portion 12. The handle portion 18 has a hollow interior in communication with the hollow interior of the head portion 12. The handle portion 18 has indentations 20 formed within a side wall thereof, which provide ergonomic handling, such that the handle portion 18 fits comfortably within the user's hand. Best seen in FIG. 5, the handle portion 18 has a motor 19 disposed therein in communication with the rotating brush groups 17 of the head portion 12 with a drive shaft 21. Each rotating brush group 17 has a drive gear 23 which meshes with the drive gear 23 of another brush group 17, or with the drive shaft 21. The motor 19 is powered by rechargeable batteries disposed within the hollow interior of the handle portion 18. The rechargeable batteries have a charging port 22 disposed within the side wall of the handle portion 18. An adapter 24 couples the charging port 22 with an electrical outlet and provides power conversion suitable for charging the rechargeable batteries. The handle portion 18 has a power switch 26 disposed within the side wall. The power switch 26 can be configured to selectively provide power to the motor 19, and to selectively control the speed of said motor 19.

The three manual pumps 28 are slidably disposed within the handle portion 18. Referring to FIG. 4, three reservoirs 40 are provided, each capable of containing a liquid substance 42. The liquid substance may be either a true liquid, or a semi-viscous liquid substance. In particular, it is contemplated that the three reservoirs 40 contain a toothpaste solution, mouthwash, and an antibacterial rinse. Filling ports 44 may be provided in the planar upper surface of the handle portion 18 which are each in direct communication with one of the reservoirs 40, so as to allow the user to refill the reservoirs 40. A filling port cap 46 selectively securable onto each filling port 44 ensures that the contents of the reservoirs 40 do not leak from the toothbrush. One of the pumps 28 is in direct communication with each of the reservoirs 40.

Referring to FIG. 4 and FIG. 5, three delivery tubes 30 extend within the head portion 12 and the handle portion 18 and deliver liquid substances from the reservoirs 40 to the outlet pumps 28. Each of three tubes 30 selectively delivers quantities of liquid toothpaste, mouthwash, and antibacterial rinse. Pressing of the manual pumps 28 will force the toothpaste, mouthwash, and rinse through the tubes 30 and out through the outlet ports 14. In particular, the pumps 28 each have a chamber 50, a piston 52, and a plunger 54. By pressing down upon the plunger 54, the user causes the piston 52 to move downward within its chamber 50, in turn causing the liquid substance to be forced outward through the delivery tube. It should be understood, however, that the pump 28 illustrated herein is simplified and is illustrative only - many other pumping mechanisms can be employed to accomplish the same purposes and meet the same requirements as described herein.

As described earlier, it is contemplated that the liquid substances include a toothpaste solution, mouthwash, and an antibacterial rinse. The primary purpose of antibacterial rinse is to sanitize the toothbrush. Accordingly, during use, the user would typically operate the pumps 28 that dispense the toothpaste and mouthwash while the toothbrush is in the mouth of said user. However, following such use and before storage of the toothbrush, the user will then operate the pump 28 which dispenses the antibacterial rinse housed in one of the reservoirs 40, to sanitize the bristles 16 and surfaces of the toothbrush which contact the mouth. In general, when dispensing any of the liquid substances, it is desirable to have the motor operating, so that the liquid substances are spread among the bristles by rotary motion of the bristle groups 17, especially if the outlet ports 14 of each brush group 17 are associated with one of the delivery tubes 30 as illustrated, which itself is associated with one of the reservoirs 40.

The carrying case 32 is adapted for holding the head portion 12, handle portion 18, adapter 24, and the three tubes 30 therein. The carrying case 32 contains a spare head portion 34 therein. Indeed, the head portion 34 can be detachable by providing adequate connection with the handle portion to properly connect the three delivery tubes 30 and the drive shaft 21. The carrying case 32 includes a handle 36 and a lock 38 to prevent unauthorized use.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A toothbrush with multiple pumping systems for cleaning teeth of a user and allowing toothpaste, mouthwash, and antibacterial rinse to be pumped independently from the toothbrush, comprising:

a head portion having a generally rectangular configuration, the head portion having a planar upper surface, a planar lower surface and a hollow interior, the planar upper surface having three rings of a plurality of outlet ports formed therein, a plurality of bristles are secured in the outlet ports;

an elongated handle portion removably coupling with the head portion, the handle portion having a hollow interior in communication with the hollow interior of the head portion, the handle portion having indentations formed within a side wall thereof for accommodating a hand of the user, the handle portion having a motor disposed therein in communication with the rotating bristles of the head portion;

three manual pumps disposed within the handle portion, each having a plunger which is operable by the user;

three reservoirs, each reservoir containing one of liquid toothpaste, mouthwash, and antibacterial rinse;

three delivery tubes removably disposed within the head portion and the handle portion disposed between the outlet ports of the head portion and the three pumps; and a carrying case adapted for holding the head portion, handle portion, adapter, and the three tubes therein, the carrying case containing a spare head portion therein.

2. A toothbrush with multiple pumping systems for allowing toothpaste, mouthwash, and antibacterial rinse to be pumped independently from the toothbrush by a user, comprising:

a head portion having a plurality of outlet ports formed in three rings, the head portion having a plurality of bristles secured within the outlet ports;

an elongated handle portion coupled with the head portion, the handle portion having a hollow interior in communication with the hollow interior of the head portion;

three reservoirs, each containing a liquid substance selected from toothpaste solution, mouthwash, and antibacterial rinse;

three manual pumps slidably disposed within the handle portion, each of the manual pumps in communication with one of the reservoirs; and three delivery tubes, each extending between the manual pumps and the outlet ports, for selectively delivering liquid substance from one of the manual pumps to the outlet ports.

3. The toothbrush with multiple pumping systems as set forth in claim 2, wherein the handle portion has indentations formed within a side wall thereof for accommodating a hand of the user.

4. The toothbrush with multiple pumping systems as set forth in claim 2, wherein the bristles are arranged in three brush groups, and further comprising a motor, the motor is mechanically linked with the brush groups for selectively rotating the brush groups.

5. The toothbrush with multiple pumping systems as set forth in claim 4, wherein each manual pump comprises a cylinder in communication with one of the reservoirs and one of the delivery tubes, a piston movable within the cylinder, and a plunger mechanically linked to the piston so that the user can push upon the plunger to operate the pump.

6. The toothbrush with multiple pumping systems as set forth in claim 5, wherein each reservoir has a fill port, and a fill port cap.

7. The toothbrush with multiple pumping systems as set forth in claim 6, wherein each of the delivery tubes is in communication with the outlet ports of one of the brush groups.

8. The toothbrush with multiple pumping systems as set forth in claim 7, further including a carrying case adapted for holding the head portion, handle portion, adapter, and the three tubes therein.

9. The toothbrush with multiple pumping systems as set forth in claim 8, wherein the carrying case contains a spare head portion therein.

* * * * *